United States Patent
Sung et al.

(10) Patent No.: US 8,067,672 B2
(45) Date of Patent: Nov. 29, 2011

(54) FLOWER TISSUE-SPECIFIC PROMOTER AND USES THEREOF

(75) Inventors: Pin-Hui Sung, Kaohsiung (TW);
Pung-Ling Huang, Taipei (TW); Yi-Yin Do, Taipei (TW)

(73) Assignee: Agriculture and Food Agency, Council of Agriculture, Executive Yuan, Nantou County (TW)

( * ) Notice: Subject to any disclaimer, the term of this patent is extended or adjusted under 35 U.S.C. 154(b) by 667 days.

(21) Appl. No.: 12/121,694

(22) Filed: May 15, 2008

(65) Prior Publication Data

US 2009/0288229 A1    Nov. 19, 2009

(51) Int. Cl.
*C12N 15/82*    (2006.01)
*C12N 15/87*    (2006.01)
*C07H 21/04*    (2006.01)

(52) U.S. Cl. .................. 800/287; 536/24.1; 800/278

(58) Field of Classification Search .................. None
See application file for complete search history.

(56) References Cited

U.S. PATENT DOCUMENTS

2004/0139501 A1 *   7/2004   Hauptmann et al. .......... 800/287
* cited by examiner

*Primary Examiner* — Li Zheng (74) *Attorney, Agent, or Firm* — Schmeiser Olsen & Watts LLP (57) ABSTRACT

A flower tissue-specific promoter, and uses thereof, is the promoter for *Phalaenopsis* 1-aminocyclopropane-1-carboxylic acid synthase, ACC synthase gene PtACS2, and has a sequence as shown in SEQ ID No: 2. The invention further provides a gene expression cassette, which is composed of a promoter having a DNA sequence as SEQ ID No: 2, and a polynucleotide with an open reading frame linked to the 3' end of said promoter, wherein said promoter can activate transcription of said polynucleotide in an organism containing said gene expression cassette. The invention provides furthermore a gene expression vector, which is composed of a promoter having a DNA sequence as SEQ ID No: 2. The invention provides further a method for producing a transgenic plant or parts of organ, tissue or cell of the transgenic plant that contain a gene expression cassette described above.

5 Claims, 3 Drawing Sheets
(1 of 3 Drawing Sheet(s) Filed in Color)

SEQUENCE LISTING

```
<160> NUMBER OF SEQ ID NOS: 10

<210> SEQ ID NO 1
<211> LENGTH: 1567
<212> TYPE: DNA
<213> ORGANISM: Phalaenopsis 'True Lady'
<220> FEATURE:
<221> NAME/KEY: CDS
<222> LOCATION: (54)...(1391)
<300> PUBLICATION INFORMATION:
<308> DATABASE ACCESSION NUMBER: Genbank/ AF004663
<309> DATABASE ENTRY DATE: 2003-10-16
```

<400> SEQUENCE: 1

```
attaatactt gtctcaatct aatctctgct atcagtaagt actaattaaa atcatgtcta      60
aaatgtttgg gaaagaggtg ccattgtcaa aaatggcggt gtctaaagct catggagagg     120
gctctccata cttcgctggc tggaaagctt atgaagagaa tcggtatgat gctgtaggaa     180
atcctgatgg agttattcag atgggcttag ctgagaatca gctttctttt gatctgctgg     240
aagagtacct ggagctgcac cctgaagctt ttagctgggc ttctgactcc tctagtttta     300
gagaaaatgc tttgtttcag gactatcatg gcctccaaac tctcagacag gcattggcta     360
gctttatgga gaaaataaga ggtggtcgat caaagttcga tgccaaccgc atcgtcctca     420
ccgccggcgc caccgccgcc aacgagatcc ttacatttat cttagccgac cgcggcgatg     480
ccttacttgt cccaactcct tattatccag ggttttgag agacctgcaa tggagaactg      540
gagtcaccat cttccccgtc cattgctaca gctccaatgg cttccaactg actctctcct     600
ccctggaaaa agcctacgct gaagccaaag cttccaactt aatgtcagg ggtcttctga      660
tgaccaatcc ttgtaatcct ctgggcacct ctgcctctct ttctcttctc caagacataa     720
ttcacttcat ctcagacaaa acattcatc tgatctccga tgagatctac tctggctctg      780
ttttctcttc tacaaactta ttcagcattt cagatctcat cactgatgcc atctctgaac     840
aagttcatat tgtttatagc ttatcgaaag atttgggcct tcctggtttc agagttggag     900
ctctgtattc ctataacgac agagttgtta aaacagcgag aagaatgtca gtttcagtc      960
ttgtttcttc tcagactcaa aggttgctgt cttttatgct gtcagatgag gagtttacag    1020
tgagatatat agagaagaat agagagagac tgagagagag atatgaatta gttgttaatg    1080
ggttgaagga agcagggatt gagtgcttga aggagaggc agggctgttc tgttgggtga     1140
atatggagaa gttgatggag gaggagacga aggaaggaga agcagagctc tggaaagtga    1200
taattgatga tttaaagctt aatatatcgc caggttcttc atgttgttgt gctgaaccag    1260
gttggttcag actttgcttt gctaatatga gcagagagac gttggaggtg gcgctgaaga    1320
gattgaagga ttttgctcag aagaaggtcg ctgctaagaa gaagaagatg aacaatgttt    1380
acttctgttg attaattaga cttagttgta cttaagttgt ttaattagtt agatgaaaaa    1440
gtaagttgta cttggttgga cactttgaga aattaatgct attttcattg gtacgtacaa    1500
gttgatatgt gagtttttag tactgtatat atcttaattg catttcatga ataaatgtt     1560
aattatt                                                              1567
```

<210> SEQ ID NO 2
<211> LENGTH: 2968
<212> TYPE: DNA
<213> ORGANISM: Phalaenopsis 'True Lady'

<400> SEQUENCE: 2

```
ctgcaggtca acggatcaaa atgttcctaa aattatattg acacgcaaga atctcggagc      60
acattttgac cgagagcttc aaaaatcaaa attagaaaca ttgtgctcta atttatgatc     120
aaatgaaggg tcctagggag acggaattga tgacataaaa aaacgatccg atccgagtta     180
attgcaccca aatcatgcac tcaaaacata attgtatgat ttgaaatata ttttggagtt     240
tgacaagtat ggtcaaatcg agtgtcttga agagctatat atcacttatt tctaacatca     300
ttaaggcgct taaatgctca tagaatgtcg tttgatcaaa gggatcagtt tgggccgttg     360
aatgaagtaa tctggattca tgtaatattt atggagcctg ctacttacaa aatctataaa     420
ttgtcctcca cctaatgcat gaaaagggaa ttgggcattg aagagaaagt tgaagaagtt     480
```

```
gcaagctctt gaggattccc gagcttcact ggtccctgaa aaacgctatc gagccgtcgc    540
gcaatcagac cactgttgct tgactaagat catagagccg ccaccacaac taggccatat    600
ttttctggac accgttgtcg ggtcagctcc accgtctgac cactgtcact tcccaaccac    660
cgccattaag tcaccgccac tgtcgaacca ccattgctcg atcattgcca tttagaccac    720
tggaccacca ttgtcttgct aacgccacca tcgaacctca gccttttgac cgtcatcacc    780
gttgtgccat tgttgtccga ccctcacctt tgcctgaccg ccgtcgctac taccaaacca    840
ccgtcgtata gccacaacca accccagacc accactacgc gcctgccatt gtcgttgagc    900
cgttccatca tcatcgggcc actgtcacca caccgaacca ttgtatgacc atcgtcagyc    960
gctagaccag tgtctcccaa cctccaatgt tgttgtactc agatcacgag cttgaaatga   1020
tactgttcct aaacataaat taaccaaaca ataagttgtt catgtttgtt tatttagtaa   1080
ttgaatactt ataaaaatgt tcaagtatgt ttatttagta attgattact tataaaattg   1140
ttctaagctt gcttaactaa ttgttcaaat gatcataaat gaactttaat caagtctagc   1200
acaattagca tgtcaaatgc acggctcatc tgcaaccttà cacaagacga ctaatgttgc   1260
caccaccaaa gctctgcttg cagaccatca tcattgtcgc cttcagacca cagtcaccac   1320
taacgacact agcatcagac tttctcgcac tcgatctcta ctaatgcctt tttattctca   1380
gcaatcgggg tcgcaaccac ttcctcaata ttttctgcc actttcctag taaaaatcac    1440
gtcccactca tgtaatattg cttctgggta ttcaaaggcg agaaagtct tgtaacatac    1500 atcagcatag cgcaatcatt tcacctgagt cggacctcat agttttgcc ccttcaaatt    1560 tttcacgtaa aaaaactctt gtcgtctttc tgtcaatttc ttttaccag aatctgtgtc    1620 agattttcgt ataacattaa gatgttaata tgtcactcta ccgccgtaaa ttaatttaat   1680
tagtatgtaa ttaattaaaa tagtatattt atttatttct ggaataataa atttatttat   1740
tgtcaatctg atagttacaa atcataacaa tgattttctg agaagccatc caagctacca   1800
tttatagaaa atgtactttt cgccccttcc cttttgaac cttatcttta ctgaatcgtc    1860
aagtcaaata cctataact catttttgct gctcaagaaa aataaaaata gagcagaaag   1920
tatgacgaac atggctctat agtgtgaaca agcttccaac ttgatcatca tctctagcac   1980
gaattctaaa gctaggacgg atttaccggc cagcatttta aatttatagt ccatctgctt   2040
acaatgcaca ccgcacaact cctatatatt tacatatttc acactcaaat tttcatattt   2100
acacttataa cactttaaaa tcataaactt atgcattaaa atatagtgat gatggtagtt   2160
ttgatgtgat gttaaaattt tgaatatata taggggttga tgtataaatg catgagaatt   2220
gtatggtatg tatgtaaatg ccgcaacaat gaattagaga agaaacgtgc atttaaaatt   2280
ttaaaaaatt atagccaaat aataaacact tctactttac tattttatgg gaataattgt   2340
acaaaaaaaa aaagggaaat ttacctacct agcacacaat tcttattgta tttacatatc   2400
tgacatctca aatctttcat atttacatac atggcacatt ggtgtgctat tttatgtgat   2460
attaaagatt tgagtgctag atctgtaaaa taagaaagtt aagatagtgt aagatatgta   2520
aatacataaa tattgtgtgc tatgtatgta aatgcccccca cccaaacaaa aaatgtagac   2580
atttactttg gagatgtagt attttctttt ttatatgcat aatgaagctg agatatcaaa   2640
ccatgaaaat atctcactgt gctgcagctc tgaaaacagc tgtctaaaca ctcagcagat   2700
aacactctcc attaaattta aaaaaagaa aaattgacag aaaaaaatta gaaccaatca   2760
ttagcttaat taaatgttaa tataattaat ttcatgcaaa tttatagtcc catgcatgac   2820
cagcttgggc tttggagccc tataaatatg agcaatgtat ggcagacaat caattccttg   2880
```

-continued tagccttctc cttcttttt ctaagtcttt ctccaattaa tacttgtctc aatctaatct    2940
ctgctatcag taagtactaa ttaaaatc    2968

<210> SEQ ID NO 3
<211> LENGTH: 18
<212> TYPE: DNA
<213> ORGANISM: artificial sequence
<220> FEATURE:
<223> OTHER INFORMATION: forward primer

<400> SEQUENCE: 3
tgcatgcatg caagcttg    18

<210> SEQ ID NO 4
<211> LENGTH: 37
<212> TYPE: DNA
<213> ORGANISM: artificial sequence
<220> FEATURE:
<223> OTHER INFORMATION: reverse primer

<400> SEQUENCE: 4
ataccatggc ccggggatcc tctagagtcg aggtcct    37

<210> SEQ ID NO 5
<211> LENGTH: 21
<212> TYPE: DNA
<213> ORGANISM: artificial sequence
<220> FEATURE:
<223> OTHER INFORMATION: forward primer

<400> SEQUENCE: 5
ataccatggt acgtcctgta g    21

<210> SEQ ID NO 6
<211> LENGTH: 22
<212> TYPE: DNA
<213> ORGANISM: artificial sequence
<220> FEATURE:
<223> OTHER INFORMATION: reverse primer

<400> SEQUENCE: 6
acggccagtg ccaagcttgc at    22

<210> SEQ ID NO 7
<211> LENGTH: 22
<212> TYPE: DNA
<213> ORGANISM: artificial sequence
<220> FEATURE:
<223> OTHER INFORMATION: forward primer

<400> SEQUENCE: 7
acactgcagg tcaacggatc aa    22

<210> SEQ ID NO 8
<211> LENGTH: 18
<212> TYPE: DNA
<213> ORGANISM: artificial sequence
<220> FEATURE:
<223> OTHER INFORMATION: reverse primer

<400> SEQUENCE: 8
tacagatcta gcactcaa    18

<210> SEQ ID NO 9
<211> LENGTH: 18

-continued

```
<212> TYPE: DNA
<213> ORGANISM: artificial sequence
<220> FEATURE:
<223> OTHER INFORMATION: forward primer

<400> SEQUENCE: 9
gagtgctaga tctgtaaa                                                  18

<210> SEQ ID NO 10
<211> LENGTH: 25
<212> TYPE: DNA
<213> ORGANISM: artificial sequence
<220> FEATURE:
<223> OTHER INFORMATION: reverse primer

<400> SEQUENCE: 10
tttagccatg gattttaatt agtac                                          25
```

FLOWER TISSUE-SPECIFIC PROMOTER AND USES THEREOF

BACKGROUND OF THE INVENTION

1. Field of the Invention

The invention relates to a stretch of gene promoter capable of activating expression specifically in plant tissue, and in particular, to a promoter capable of activating expression specifically in calyx, petal and stamen of a plant floral organ, as well as to the application of said promoter.

2. Description of the Prior Art

In transgenic plants, the target gene to be transferred into the plant has to be constructed downstream of a promoter usable by the plant. After transformation, the expression of said target gene in the transgenic plant can be activated by the action of said promoter. The CaMV 35S promoter is the most commonly used promoter for driving target gene expression in plants. However, CaMV 35S promoter does not exhibit tissue specificity, and hence can not carry out the expression of the target gene in a specific plant tissue to achieve the purpose of modulating a gene expression. Further, it exhibits lower activity in monocot plants, such as orchid, than in dicot plants.

In some cases, constitutive over-expression of a transgenic target gene may interfere with the normal physiological processes in a plant. The development of tissue-specific promoters to drive a particular gene of interest should help to alleviate these problems. Therefore, the isolation and development of floral specific promoters from monocots is necessary. To modulate the expression of a target gene in transgenic plants, the critical point for modulating a gene expression is how to make a strong expression of a target gene at a specific tissue organ and/or a specific phase other than carrying out a strong expression of a target gene in the transgenic plant. Therefore, one of the important topics in promoting industrial development is to screen each promoter with different a specificity that can be used as various tools for modulating gene expression so that the transferred promoter can support the production of recombinant protein, as well as a promoter having activating ability with space specificity so as to attain the function of modulating gene expression and hence increase economical benefit.

In view of the foregoing, it is evident that CaMV 35S promoter has many disadvantages, is not designed perfectly and needs to be urgently improved.

The inventor had recognized various disadvantages derived from the conventional CaMV 35S promoter described above, and had devoted to improve and innovate. After studying intensively for many years, the inventor has developed a promoter capable of activating expression specifically in a floral organ tissue according to the invention and the application thereof.

SUMMARY OF THE INVENTION

Accordingly, one object of the invention is to provide a promoter capable of activating expression specifically in a floral organ tissue, wherein the sequence of said promoter is derived from the promoter PtACS2 (GeneBank accession number AF004663, SEQ ID No: 1) for gene of 1-aminocyclopropane-1-carboxylic acid synthase (ACC synthase) of *Phalaenopsis* True Lady. In the invention, the cDNA from ACC synthase gene PtACS2 of *Phalaenopsis* True Lady is used as a probe, a plaque hybridization reaction is carried out on the genomic DNA library of *Phalaenopsis*, and, after several purifications, a *Phalaenopsis* ACC synthase genomic clone is obtained. Nucleic acid sequencing shows a 2,968 bp local sequence (SEQ ID No: 2) ahead of the translation start site (gene code: ATG) of *Phalaenopsis* ACC synthase gene PtACS2. That sequence is used as the promoter of *Phalaenopsis* ACC synthase gene PtACS2.

In order to analyze whether said *Phalaenopsis* ACC synthase gene PtACS2 promoter (SEQ ID No: 2) exhibits tissue specificity, the sequence of that promoter is ligated to the 5' end of the sequence of a reporter gene, β-glucuronidase (GUS) gene such that the promoter can act as the promoter of said reporter gene. Then, the assembly of the promoter and the reporter gene is constructed into an *Agrobacterium* transformation vector to form a plasmid pPtACS2-GUS. Thereafter, by using *Agrobacterium* transformation process, said plasmid pPtACS2-GUS is transformed into model plants, *Arabidopsis thialana* and *Nicotiana tabacum* L., respectively. The activating activity of said gene promoter is assayed then by means of histochemical staining of GUS. The result shows that said *Phalaenopsis* ACC synthase gene PtACS2 promoter (SEQ ID No: 2) enables the gene activated thereby to be expressed specifically in a floral organ tissue of a plant. Therefore, the activating ability of the *Phalaenopsis* ACC synthase gene PtACS2 promoter (SEQ ID No: 2) according to the invention exhibits extreme tissue specificity.

In addition to providing a promoter capable of activating expression specifically in a floral organ tissue, the invention provides further a gene expression cassette. Said gene expression cassette comprises: (1) the promoter sequence (SEQ ID No: 2) according to the invention, and (2) a polynucleotide with an open reading frame (ORF), namely, a target gene. Said polynucleotide is attached to the 3' end of the inventive promoter. Said promoter can start the transcription of said polynucleotide in an organism having said gene expression cassette. In a preferred embodiment, said target gene is a reporter gene, β-glucuronidase (GUS) gene.

Furthermore, by constructing the inventive *Phalaenopsis* ACC synthase gene PtACS2 promoter (SEQ ID No: 2) into a commercial transformation vector such as, but not limited to: pBI101 (ClonTech), pBI121 (ClonTech), pBIN 19 (GenBank Accession No: U09365), pCAMBIA1301, pCAMBIA1305, pGREEN (GenBank Accession No: AJ007829), pGREEN II (GenBank Accession No: EF590266) (John Innes Centre), pGreen0029 (John Innes Centre), or pCLEAN (John Innes Centre), a gene expression vector can be formed. Alternatively, a target gene can be inserted in said gene expression vector in a manner that, after attaching said target gene to the 3' end of the inventive promoter, a gene expression cassette described above can be formed. Moreover, through a transformation process, the inventive promoter together with the target gene attached downstream to its 3' end can be transformed into a plant of interest. Further, the genomic constitution of the transgenic plant can be altered such that the inventive promoter together with the target gene can activate effectively the expression of said target gene in the objective transgenic plant and its progeny as well.

In another aspect, the invention further provides a process for producing a transgenic plant or parts of organ, tissue or cell of the transgenic plant comprising the above-mentioned gene expression cassette; said process is composed of the following steps:

step 1: taking cells or tissues of an objective plant;

step 2: transforming a gene expression cassette containing the inventive promoter sequence (SEQ ID No: 2) into cells or tissues of the objective plant obtained in step 1 to give a transgenic plant cell or transgenic plant tissue; and step 3: cultivating the transgenic plant cell or transgenic plant tissue obtained in step 2 to give a transgenic plant or part of organ, tissue or cell of said transgenic plant having gene expression cassette containing the inventive promoter sequence (SEQ ID No: 2);

wherein the transformation method described in step 2 includes, but not limited to, *Agrobacterium* mediating method, gene recombinant virus infection method, transposon vector transformation method, gene gun transformation method, electroporation, micro-injection method, pollen tube pathway, liposome-mediated transformation method, ultrasonic-mediated transformation method, silicon carbide fiber-mediated transformation, electrophoresis, laser microbeam, polyethylene glycol (PEG), calcium phosphate transformation, DEAE-dextran transformation and the like.

These features and advantages of the present invention will be fully understood and appreciated from the following detailed description of the accompanying Drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 shows results of the expression analysis for reporter gene β-glucuronidase (GUS) at various tissue sites in the progeny of *Arabidopsis* thialana transformant containing PtACS2p::GUS-NOS gene expression cassette.

FIG. 4 shows results of the expression analysis for reporter gene β-glucuronidase (GUS) at various tissue sites in the progeny of *Nicotiana tabacum* L. transformant containing PtACS2p::GUS-NOS gene expression cassette.

DETAILED DESCRIPTION OF THE PREFERRED EMBODIMENT

Example 1

Cloning of *Phalaenopsis* ACC Synthase Gene PtACS2 Promoter

1. The Sources of *Phalaenopsis* λEMBL3 Genomic Library

*Phalaenopsis* genomic library was prepared by extracting genomic DNA from leaves of a white with red lip *Phalaenopsis* True Lady, and then carrying out the construction of a genomic library through enzyme digestive replacement of DNA fragment by using bacteriophage λEMBL3 as the vector.

2. Preparation and Labeling of a Nucleic Acid Probe

A nucleic acid probe was prepared by using cDNA (with sequence as shown in SEQ ID No: 1) of *Phalaenopsis* ACC synthase gene PtACS2 (GeneBank accession number AF004663) as the template of the probe, carried out a process based on the principle of random primer labeling by means of Prime-a-gene kit (Stratagene). The total reaction volume was 50 μL, and the reaction mixture contained 1.2 μg/mL of a single-strand DNA fragment, 400 μg/mL of BSA, 20 μM dNTP (dAT P, dTTP, dGTP), 1 × labeling buffer, 50 μCi [α-$^{32}$P] dCTP, 5 units of Klenow DNA polymerase. It was allowed to react at 37° C. for more than 1 hour. Thereafter, the reaction was terminated by addition of 2 μL of 0.5 M EDTA-Na$_2$ (pH 8.0). Then, 8 μL of tracing dye (50% glycerol, 0.25% bromophenol blue) was added thereto. The reaction solution was passed through a Sephadex-G50 chromatographic column eluting with TE (pH 7.6), and fractions were collected in tubes. Then, the radioactivity of fractions thus collected was measured on a Liquid Scintillation Counter (Beckman 1801). Fractions collected from the first peak with strongest radioactivity were used as the probe.

3. Screening of *Phalaenopsis* ACC Synthase from Genomic Library

*Phalaenopsis* genomic library was screened by means of plaque hybridization to give 1.5 million plaque forming units. At first, bacteriophages were diluted serially with SM (100 mL SM, containing 0.58 g NaCl, 0.2 g MgSO$_4$.7H$_2$O, 5 mL Tris-HCl and 0.01 g gelatin). Then, host cells (*Escherichia coli* XL1-Blue MRA (P2)) was added thereto and incubated in a water bath at 37° C. for 15 minutes. Thereafter, it was mixed homogeneously with top agarose (each liter containing 5 g NaCl, 2 g MgSO$_4$.7H$_2$O, 5 g Bacto-Yeast extract, 10 g NZ amine A, 7 g Agarose, pH 7.5), applied over NZY solid culture medium (each liter containing 5 g NaCl, 2 g MgSO$_4$.7H$_2$O, 5 g yeast extract) and incubated at 37° C. for 8~10 hours. After this time, the bacteriophages were transferred to nitrocellulose membrane. The membrane was treated successively in denaturing buffer (0.5 M NaOH, 1.5 M NaCl) for 2 minutes, neutral buffer (0.5 M Tris-HCl, 1.5 M NaCl, pH 7.5) for 5 minutes, and 2 ×SSPE (0.36 M NaCl, 20 mM NaH$_2$PO$_4$.H$_2$O, 2 mM EDTA, pH 7.4) for 30 seconds. Then, after treated in a vacuum oven at 80° C. for 2 hours, the membrane was placed in 2 ×SSPE and 0.1% SDS solution, and was shaken at room temperature for 1 hour. Thereafter, it was placed in a pre-hybridizing solution (5 ×SSPE, 0.1% SDS, 5 ×BFP (0.1% BSA, 0.1% Ficoll, 0.1% Polyvinyl pyrrolidone), 30% Formamide, 500 μg/mL of denatured salmon sperm DNA) and allowed to react at 37° C. for more than 2 hours. After the pre-hybridizing reaction, the membrane was placed in a hybridizing solution (5 ×SSPE, 0.1% SDS, 1 × BFP, 30% Formamide, 100 μg/mL of denatured salmon sperm DNA and denatured probe solution), and allowed to react at 37° C. for 16~18 hours. Then, the membrane was treated twice in a washing solution 1 (5 ×SSPE, 0.1% SDS) at room temperature for 15 minutes, and then treated twice in a washing solution II (1 ×SSPE, 0.5% SDS) at 37° C. for 15 minutes. After these treatments, it exposed to X-ray film (Kodak XAR film) at −80° C. After development, bacteriophages containing target gene DNA could be detected from the X-ray film. The corresponding bacteriophage plaque was picked up into SM containing 0.03% chloroform and was shaken slightly for 1 hour. It was then stored at 4° C. After several purifications, a target clone λOTACS1 could be obtained.

4. Mass Replication of Bacteriophages

The bacteriophage liquor of the above-described objective clone λOTACS1 was placed over NZY solid culture medium and the bacteriophage liquor was gashed with a toothpick. 3 mL Top agar incorporated with host cell, *E. coli* XL1-Blue MRA (P2), was added and was cultured over NZY solid culture medium at 37° C. for 8 hours. On the next day, the single plaque agar lump on the gashed line was picked up with a capillary. The agar lump was spread and cultured over NZY solid culture medium at 37° C. for 7-11 hours. Then, the culture medium was transferred into a refrigerator at 4° C., where SM was added to dissolve out bacteriophages. The solution thus obtained was collected into a centrifuge tube. Chloroform was added up to 0.03%. The mixture was then centrifuged at 4° C. 7,000 rpm (Beckman J2-MC, JS-13.1) for 5 minutes, and was placed at 4° C. for future extraction of bacteriophage DNA.

5. Extraction of Bacteriophage DNA

Host cell *E. coli* XL1-Blue MRA (P2) was cultured and concentration of host cells in the culture suspension was adjusted to $OD_{600}$ of 0.5. This was placed in ice till used. Bacteriophages of the objective clone λOTACS1 thus mass replicated above were mixed with host cells (count ratio of bacteriophages:host cell=5:1) in 1 mL SM and 5 mL of 2.5 mM $CaCl_2$. The resultant mixture was allowed to stand at room temperature for 15 minutes. After this time, it was treated at 37° C. for 45 minutes and was added then thereto 100 mL of 2 ×NZY liquid culture medium (0.4% $MgSO_4.7H_2O$, 2% NaCl, 1% bacto-yeast extract, 2% NZ amine, 0.2% casaimino acid, 5 mM $MgSO_4$, 25 mM Tris-HCl, pH 7.5). The mixture was incubated at 37° C. 240 rpm for more than 8 hours. Then, 4.5 mL Chloroform was added, followed by incubation at 37° C. 240 rpm for 15 minutes. Thereafter, it was centrifuged at 4° C. 5,000 rpm (Beckman J2-MC, JS-13) for 20 minutes. The supernatant was poured in another centrifuge tube and 100 μL DNase I (1 mg/mL) and 100 μL RNaseA (10 mg/mL) was added thereto. The resultant mixture was treated at 37° C. 80 rpm for 45 minutes. Next, 33 mL of 4 M NaCl was added and placed in an ice-water bath for 1 hour. After adding 33 mL of 50% polyethylene glycol, it was treated at 4° C. for more than 4 hours, then centrifuged at 5,000 rpm for 20 minutes (Beckman J2-MC, JA-10). The supernatant was removed completely, and the pellet was suspended in 500 μL of PKB solution (10 mM NaCl, 10 mM Tris-HCl, pH 8.0, 10 mM EDTA, 0.1% SDS). To the suspension thus obtained, proteinase K (final 12.5 μg/mL) was added and allowed to react at 37° C. for 20 minutes. The upper layer was extracted with a mixed solvent of equal volume of phenol, PCI (phenol:chloroform:isoamyl alcohol=25:24:1) and CI (chloroform:isoamyl alcohol=24:1). Thereafter, 2-fold volume of 100% ethanol (−20° C.) was added and mixed homogeneously. DNA was picked up and rinsed by immersing in 70% ethanol and 100% ethanol. After being air-dried, it was re-dissolved in 100 μL TE (pH 7.5). Its DNA concentration was determined by $OD_{260}$, and then stored at 4° C. till used for DNA sequencing.

6. DNA Sequencing

Figures 1A, 1B:
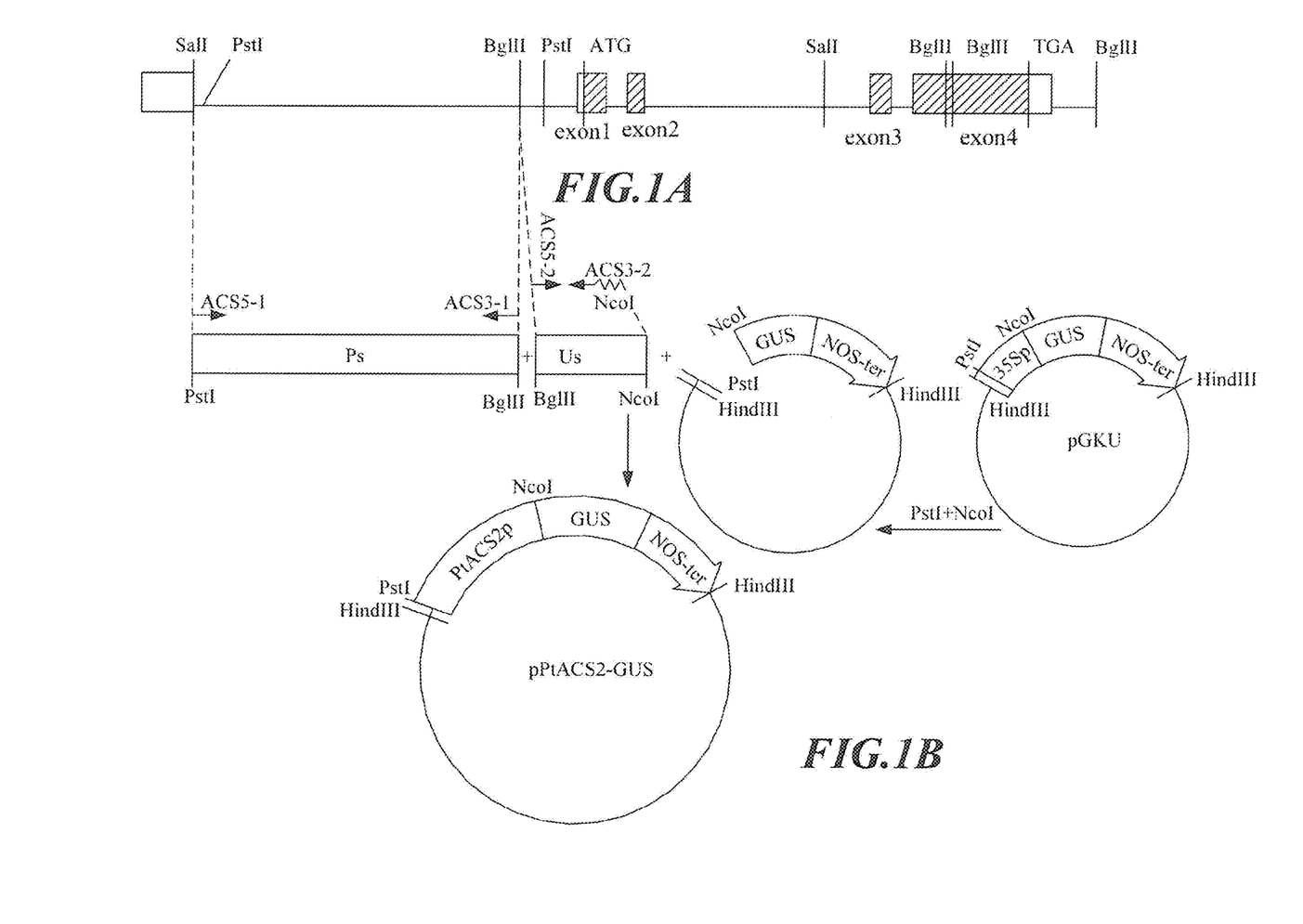
FIG. 1A is the restriction enzyme map of the genome of the inventive *Phalaenopsis* ACC synthase gene PtACS2.
FIG. 1B shows the construction strategy for the plasmid pPtACS2-GUS containing the inventive *Phalaenopsis* ACC synthase gene PtACS2 promoter.

DNA of the objective clone λOTACS1 extracted as described above was subjected to DNA sequencing by means of an automatic nucleic acid sequencer ABI sequencer 377 to give the genomic sequence of *Phalaenopsis* ACC synthase gene PtACS2 and was analyzed with PC/Gene software package from IntelliGenetics Inc. The result was shown in FIG. 1A. As shown in FIG. 1A, *Phalaenopsis* ACC synthase gene PtACS2 contained four exons, and has its translation start site (gene code: ATG) located at 54~56 nucleotides of the exon 1. Ahead of said translation start site of *Phalaenopsis* ACC synthase gene PtACS2 genomic clone λOTACS1, there was a 2,968 bp promoter region, with a sequence of said promoter region as shown in SEQ ID No: 2.

Example 2

Construction of a Vector Containing *Phalaenopsis* ACC Synthase Gene PtACS2 Promoter The construction strategy of a vector containing *Phalaenopsis* ACC synthase gene PtACS2 promoter was shown in FIG. 1B. A 2,968 bp local sequence (SEQ ID No: 2) ahead of the translation start site of *Phalaenopsis* ACC synthase gene PtACS2 was used as the *Phalaenopsis* ACC synthase gene PtACS2 promoter (PtACS2p). Said promoter (PtACS2p) was constructed into the *Agrobacterium* transformation vector pGKU to replace the original CaMV 35S promoter (35Sp) in a manner that the 3' end of the *Phalaenopsis* ACC synthase gene PtACS2 promoter (PtACS2p) sequence was linked to the 5' end of the reporter gene β-glucuronidase (β-glucuronidase, GUS) gene sequence, so as to be used as the promoter for said reporter gene.

Step 1: Construction of *Agrobacterium* Transformation Vector pGKU

Figure 2:
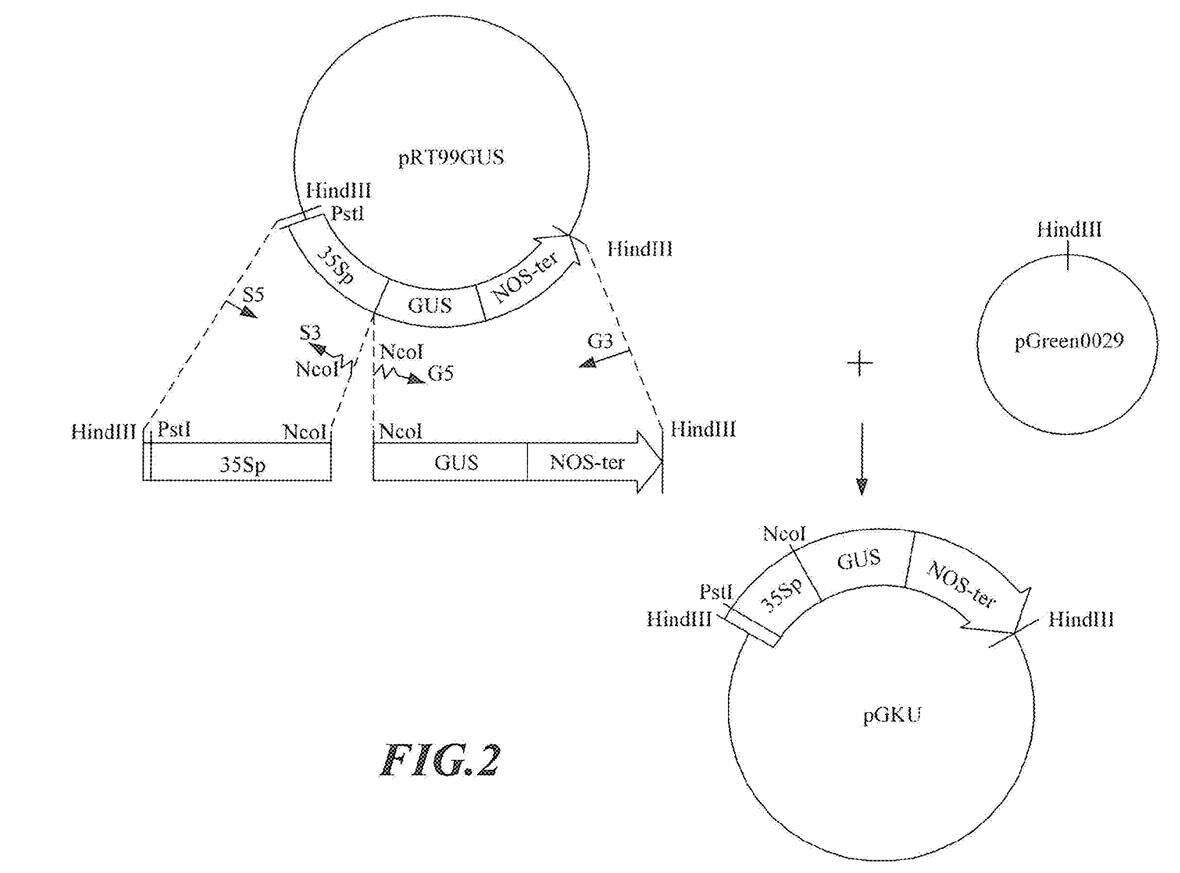
FIG. 2 shows the construction strategy for *Agrobacterium* transformation vector pGKU.
Figure 3A:
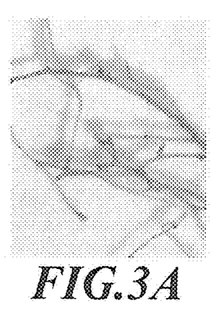
FIG. 3A: root.
Figure 3B:
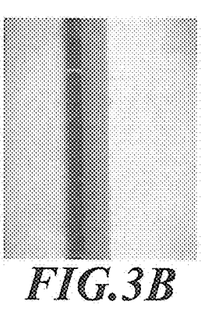
FIG. 3B: stem.
Figure 3C:
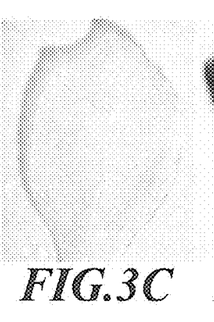
FIG. 3C: leaf.
Figure 3D:
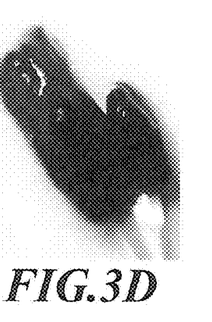
FIG. 3D: floral organ (including petal, calyx and stamen).
Figure 4A:
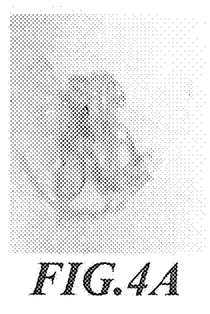
FIG. 4A: root.
Figure 4B:
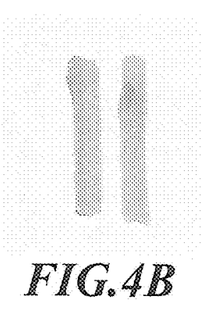
FIG. 4B: stem.
Figure 4C:
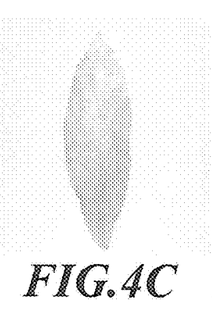
FIG. 4C: leaf.
Figure 4D:
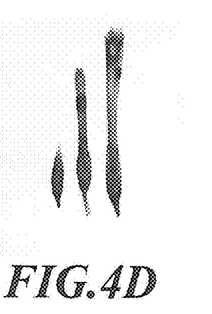
FIG. 4D: floral organ (including petal, calyx and stamen).

The construction strategy of *Agrobacterium* transformation vector pGKU was shown in FIG. 2. A fragment (CaMV 35S::GUS-NOS) was taken from the CaMV 35S promoter (35Sp)-reporter gene (GUS)-terminator (NOS-ter) of a commercial vector pRT99GUS (Töpfer et al., 1988), and was constructed into a commercial transformation vector pGreen0029 (John Innes Centre) for *Agrobacterium* to give a transformation vector pGKU. The construction strategy involved the synthesis of a CaMV 35S promoter (35Sp) DNA fragment and a reporter gene (GUS)-terminator (NOS-ter) DNA fragment by means of polymerase chain reaction (PCR), respectively. Through the design of PCR primer, NcoI restriction site was created at the 3' end of CaMV 35S promoter (35Sp) DNA fragment and the 5' end of reporter gene (GUS)-terminator (NOS-ter) DNA fragment, respectively. Finally, these two PCR synthetic fragments were constructed into pGreen0029 to give *Agrobacterium* transformation vector pGKU.

Step 1.1: Obtaining CaMV 35S Promoter (35Sp) Fragment from a Commercial Vector pRT99GUS The DNA of a commercial vector pRT99GUS was used as a template to carry out the amplification of DNA sequence of CaMV 35S promoter (35Sp) by PCR. Primers used in the PCR were as followed:

Forward Primer S5 (Containing the HindIII Restriction Site):

```
5'-TGCATGCATGC AAGCTTG-3'          (SEQ ID No: 3)
            HindIII
```

Reverse Primer S3 (Containing the NcoI Restriction Site):

```
                                   (SEQ ID No: 4)
5'-ATA CCATGGCCCGGGGATCCTCTAGAGTCGAGGTCCT-3'
       NcoI
```

Total volume of PCR reactant was 50 μl (consisting of: 1 μl genomic DNA, 10 μl of 5 × Phusion HF buffer, 1 μl of 10 mM dNTP, 1 μl of 20 μM forward primer, 1 μl of 20 μM reverse primer, 35.5 μl sterile water, 0.5 μl Phusion DNA polymerase) and PCR conditions were: 98° C. for 30 seconds, then 35 cycles at 98° C. for 10 seconds, 60° C. 30 seconds, and 72° C. 60 seconds, and finally, 72° C. for 10 minutes for elongation. PCR product of 544 bp in length was synthesized. This PCR product was digested with restriction enzymes HindIII and NcoI and a DNA fragment (fragment S) of 470 bp in length was recovered, which was stored at 4° C. until used.

Step 1.2: Obtaining Reporter Gene (GUS)-Terminator (NOS-Ter) Fragment from a Commercial Vector pRT99GUS Similarly, the DNA of a commercial vector pRT99GUS was used as the template in the PCR for the amplification of the DNA sequence of a reporter gene (GUS)-terminator (NOS-ter). Primers used in the PCR were as followed:

Forward Primer G5 (Containing NcoI Restriction Site):

```
5'-ATACCATGGTACGTCCTGTAG-3'    (SEQ ID No: 5)
     NcoI
```

Reverse Primer G3 (Containing HindIII Restriction Site):

```
5'-ACGGCCAGTGCCAAGCTTGCAT-3'    (SEQ ID No: 6)
              HindIII
```

Total volume of PCR reactants was 50 μl (consisting of: 1 μl genomic DNA, 10 μl of 5 × Phusion HF buffer, 1 μl of 10 mM dNTP, 1 μl of 20 μM forward primer, 1 μl of 20 μM reverse primer, 35.5 μl sterile water, 0.5 μl Phusion DNA polymerase) and PCR conditions were: 98° C. 30 seconds, then 35 cycles at 98° C. for 10 seconds, 60° C. 30 seconds, and 72° C. 60 seconds, and finally, 72° C. 10 minutes for elongation. A PCR product of 2,108 bp in length was synthesized. The PCR product was digested with HindIII and NcoI restriction enzymes and a DNA fragment (fragment G) of 2,093 bp in length was recovered, which was stored at 4° C. till used.

Step 1.3: Ligation of DNA

A commercial vector pGreen0029 was digested with HindIII restriction enzyme to recover a DNA fragment (fragment P) of 4,632 bp. This fragment was subjected to DNA ligation with fragment S and fragment G obtained in the above steps 1.1 and 1.2, respectively, to give transformation vector pGKU. As shown in FIG. 2, in addition to pGreen feature, transformation vector pGKU contained: CaMV 35S promoter (35Sp)-reporter gene (GUS)-terminator (NOS-ter) DNA fragment of a commercial vector pRT99GUS, and also HindIII and PstI restriction sites at the 5' end of CaMV 35S promoter (35Sp) as well as NcoI restriction site at the 3' end of CaMV 35S promoter (35Sp), such that *Agrobacterium* transformation vector pGKU could replace CaMV 35S promoter (35Sp) with other promoter sequence into the promoter of the reporter gene (GUS) by using restriction enzymes such as HindIII, PstI, NcoI and the like.

Step 2: Obtaining the Sequence of *Phalaenopsis* ACC Synthase Gene PtACS2 Promoter (PtACS2p)

A 2,968 bp local sequence (SEQ ID No: 2) ahead of the translation start site of *Phalaenopsis* ACC synthase gene PtACS2 was used as the *Phalaenopsis* ACC synthase gene PtACS2 promoter PtACS2p. As shown in FIG. 1B, a DNA fragment (fragment Ps) of 2,484 bp in length at the 5' end and a DNA fragment (fragment Us) of 495 bp in length at the 3' end of *Phalaenopsis* ACC synthase gene PtACS2 promoter (PtACS2p) were obtained through PCR. Further, by means of the design of PCR primers, a NcoI restriction site was incorporated at the 3' end of the fragment Us for subsequent construction.

Step 2.1: Obtaining a DNA Fragment (Fragment Ps) of 2,484 bp in Length from the 5' End of *Phalaenopsis* ACC Synthase Gene PtACS2 Promoter (PtACS2p)

Genomic DNA extracted from the leaf of white with red lip *Phalaenopsis* True Lady was used as the template to carry out PCR for the amplification of fragment Ps DNA sequence. Primers used in PCR were as followed:

Forward Primer ACS5-1 (Containing PstI Restriction Site):

```
5'-ACACTGCAGGTCAACGGATCAA-3'    (SEQ ID No: 7)
      PstI
```

Reverse Primer ACS3-1 (Containing BglII Restriction Site):

```
5'-TACAGATCTAGCACTCAA-3'    (SEQ ID No: 8)
      BglII
```

Total volume of PCR was 50 μl (consisting of: 1 μl genomic DNA, 10 μl of 5 × Phusion HF buffer, 1 μl of 10 mM dNTP, 1 μl of 20 μM forward primer, 1 μl of 20 μM reverse primer, 35.5 μl sterile water, 0.5 μl Phusion DNA polymerase). PCR conditions were: 98° C. for 30 seconds, 35 cycles of 98° C. for 10 seconds, 60° C. for 30 seconds, and 72° C. for 60 seconds, and finally, 72° C. for 10 minutes for elongation. A PCR product of 2,490 bp in length was synthesized. The PCR product was digested with PstI/BglII restriction enzyme. A DNA fragment (fragment Ps) of 2,484 bp in length was obtained and was stored at 4° C. till used.

Step 2.2: Obtaining DNA Fragment (Fragment Us) of 495 bp in Length from the 3' End of *Phalaenopsis* ACC Synthase Gene PtACS2 Promoter (PtACS2p)

In a similar manner, genomic DNA extracted from the leaf of white with red lip *Phalaenopsis* True Lady was used as the template to carry out PCR for the amplification of fragment Us DNA sequence. Primers used in PCR were as followed:

Forward Primer ACS5-2 (Containing BglII Restriction Site):

```
5'-GAGTGCTAGATCTGTAAA-3'    (SEQ ID No: 9)
          BglII
```

Reverse Primer ACS3-2 (Containing NcoI Restriction Site):

```
5'-TTTAGCCATGGATTTTAATTAGTAC-3'    (SEQ ID No: 10)
       NcoI
```

Total volume of PCR was 50 μl (consisting of: 1 μl genomic DNA, 10 μl of 5 × Phusion HF buffer, 1 μl of 10 mM dNTP, 1 μl of 20 μM forward primer, 1 μl of 20 μM reverse primer, 35.5 μl sterile water, 0.5 μl Phusion DNA polymerase). PCR conditions were: 98° C. for 30 seconds, then 35 cycles of 98° C. for 10 seconds, 60° C. for 30 seconds, and 72° C. for 60 seconds, and finally, 72° C. for 10 minutes for elongation. PCR product of 505 bp in length was synthesized. The PCR product was digested with BglII and NcoI restriction enzymes. A DNA fragment (fragment Us) of 495 bp in length was recovered and stored at 4° C. till used.

Step 3: DNA Ligation

*Agrobacterium* transformation vector pGKU obtained in step 1 was digested with PstI/NcoI double restriction enzymes. The digested vector pGKU was recovered, which was then subjected to a DNA ligation with fragment Ps and fragment Us obtained in step 2.1 and step 2.2, respectively, to give a plasmid pPtACS2-GUS containing promoter sequence (SEQ ID No: 2) of *Phalaenopsis* ACC synthase gene PtACS2. In said plasmid pPtACS2-GUS, a DNA sequence of a reporter gene β-glucuronidase (GUS) (PtACS2p::GUS-NOS) was linked at the 3' end of *Phalaenopsis* ACC synthase gene PtACS2 promoter. Consequently, after transforming said plasmid pPtACS2-GUS in a plant through *Agrobacterium tumefaciens* infiltration, analysis for the mode to start the expression of the reporter gene β-glucuronidase (GUS) gene by the *Phalaenopsis* ACC synthase gene PtACS2 promoter could be carried out.

Example 3

Transformation of *Arabidopsis thialana* by *Agrobacterium*-Mediated Transformation Method By using a model plant *Arabidopsis thialana* ecotype Columbia as starting material and employing *Agrobacterium* transformation, plasmid pPtACS2-GUS obtained in Example 2 was transformed into *Arabidopsis thialana* to change the genomic constitution of the transgenic plant such that *Phalaenopsis* ACC synthase gene PtACS2 promoter could start effectively the expression of the reporter gene GUS in the objective transgenic plant and also in progeny thereof. The expression site of the reporter gene GUS in *Arabidopsis thialana* transformant was analyzed by means of histochemical staining of GUS to detect whether *Phalaenopsis* ACC synthase gene PtACS2 promoter exhibited tissue specificity.

1. Preparation of *Agrobacterium* Liquor

The *Agrobacterium tumefaciens* EHA105 was inoculated in YEB solid medium (5 mg/L yeast extract, 10 g/L peptone, 10 g/L NaCl, 15 g/L Agar, pH 7.2) containing 100 μg/mL Rifamycin SV. After culturing at 28° C. for 2 days, a single colony was picked up and inoculated in 20 mL YEB liquid culture medium containing 100 μg/mL Rifamycin SV. The mixture was cultured at 28° C. under shaking at 240 rpm for 1 day. To 5 mL bacterial suspension thus cultured for 1 day, 200 mL YEB liquid medium containing 100 mg/L Rifamycin SV was added, and cultured at 28° C. under shaking at 240 rpm to $OD_{600}$ value of 0.5-0.8. The resulting suspension was centrifuged at 4° C., 4,200 rpm for 20 minutes (Beckman J2-MC, JA-10). After removing supernatant, the bacteria pellet was re-suspended in 200 mL pre-chilled sterile water. The centrifuging step described above was repeated once, the pellet was suspended in 100 mL sterile water, and then centrifuged again. The bacteria pellet was suspended in 50 mL sterile water, and one final centrifuging was carried out. The bacteria pellet was suspended in 2 mL pre-chilled 10% (v/v) glycerol, and dispended into units of 50 μl, which were stored at −80° C. till used.

2. Transformation of *Agrobacterium*

The frozen *Agrobacterium* cell described above was thawed, and 100 ng of the plasmid pPtACS2-GUS DNA obtained in Example 2 and 100 ng of a helper plasmid DNA (Soup DNA) were added thereto. In water bath, the plasmid DNA and *Agrobacterium* were mixed homogeneously, transferred into an electroporation cuvette, and subjected to electroporation under conditions of 1.44 KV amplitude, 99 μsec pulse width, for 10 pulses. After completion of electroporation, 1 mL 28° C. YEB liquid culture medium was added, and all of the liquid was drawn into a small test tube, followed by incubating at 28° C. for 1 hour. An appropriate amount of bacterial suspension was taken out, applied over a medium containing antibiotics and cultured at 28° C. for two days.

3. Mini-Preparation of *Agrobacterium* Plasmid after Transformation

A single colony of *Agrobacterium* transformant containing plasmid pPtACS2-GUS prepared in Example 2 was used to inoculate in 50 mL YEB liquid culture medium incorporated with 100 μg/mL of Rifamycin SV and 50 μg/mL of Kanamycin, and was incubated at 28° C. by shaking at 240 rpm for 2 days. The whole bacteria suspension was transferred in a 500 mL centrifuge tube, chilled over ice for 5-15 minutes, and then centrifuged at 4° C., 3,700 rpm for 10 minutes (Beckman J2-MC, JS-13.1). The supernatant was discarded, and bacteria pellet was suspended in 1 mL pre-chilled TE (pH 8.0). The resulting suspension was transferred in a 1.5 mL micro-centrifuge tube, and centrifuged at room temperature, at 14,000 rpm for 1 minute. The supernatant was discarded, 200 μL lysozyme [25 mg/mL in GTE (25 mM Tris-HCl, pH 8.0, 10 mM $Na_2EDTA$, 50 mM glucose)] was added. After mixed homogeneously by shaking at room temperature for 3-5 minutes, fresh 400 μL NaOH/SDS (0.2 N NaOH, 1% SDS) was added, mixed and placed on ice for 7 minutes. Then, 300 μL of 3 M potassium acetate was added, mixed homogeneously and placed on ice for 12 minutes. Thereafter, the suspension was centrifuged at 4° C., 13,200 rpm for 5 minutes. 800 μL of the supernatant was drawn into a micro-centrifuge tube containing 500 μL ice-cold isopropanol, and mixed homogeneously. After centrifuged at 4° C., 13,200 rpm for 10 minutes, the supernatant was discarded, and the pellet was suspended in 135 μL TE (pH 8.0). Next, 100 μL of phenol/chloroform/IAA, and 100 μL CI was added, and centrifuged at 14,000 rpm for 2 minutes. The upper clear solution was drawn into a new micro-centrifuge tube for purifying DNA. 100 μL of 4 M $NH_4OAc$ and 400 μL of 100% ethanol were added to precipitate DNA. Finally, the remaining salt was washed off with 200 μL of 70% ethanol, and 200 μL of 100% ethanol, followed by dissolving in 10 μL sterile water containing 0.1 mg/mL RNaseA. Then, the resulting solution was subjected to restriction enzyme digestion and analysis to check if successfully cloned.

4. Growth of *Arabidopsis thialana*

Seeds of *Arabidopsis thialana* were sowed in a medium consisting of peat mosses:vermiculite #3:Perlite # 3 in a ratio of 8:1:1, and was covered with a mesh. Cultivation was carried out in a growth box at 23° C., 16 hours light/8 hours dark, and 75% humidity. As the second pair of leaves was grown, 1,000 ppm HYPONeX2 (The HYPONeX Corp., OH, USA) was applied once every two weeks. After about 3-4 weeks, the plant was pruned. As the rachis had grown to a length of about 7-15 cm after 2 or 3 pruning operations, the plant was subjected to transformation.

5. Transformation of *Arabidopsis thialana*

Three days prior to transformation of *Arabidopsis thialana*, *Agrobacterium* that had been transfected and hence contained plasmid pPtACS2-GUS prepared in Example 2 was inoculated in 10 mL YEB culture medium containing 100 μg/mL Rifamycin SV and 50 μg/mL Kanamycin. The resulting suspension was cultured at 28° C. by shaking at 240 rpm for 2 days. To the 5 mL of the bacteria suspension thus obtained, 500 mL YEB liquid culture medium containing 100 μg/mL Rifamycin SV and 50 μg/mL Kanamycin was added. After incubation at 28° C. shaking at 240 rpm for 1~2 day, the suspension was centrifuged at 4° C., 6,000 rpm for 10 minutes (Beckman J2-MC, JA-10). The supernatant was discarded and the bacteria pellet was suspended in 200 mL infiltration medium (½ MS basal medium, 5% sucrose, 2 mg/mL BA, 0.01% Silwet L-77, pH 5.7 with 1 M KOH), which was stored on ice till used. On the day of transformation, blossoming floweret and siliques were removed. The plant was placed upside down in a 250-mL baker containing *Agrobacterium* liquor in a manner that all flowerets were soaked therein for several seconds and this procedure was repeated 3 times over a period of 20 seconds. Alternatively, the infiltration could be carried out by suction at 40 mmHg vacuum for *Arabidopsis thialana* Columbia was then removed and kept wet for 1 minute. The plant thus treated was grown under normal conditions. Upon siliques being dehiscent, they were bagged. Three weeks after being bagged, its seeds were harvested.

6. Screening of Transformant

Appropriate amount of seeds of *Arabidopsis thialana* Columbia thus harvested was weighed in a 15-mL centrifuge tube, soaked with fresh water for 30 minutes, followed by rinsing 2-3 times with sterile water and then treated with 10 mL of 20% bleach containing 0.05% Tween-20 by shaking vigorously for 15 minutes. The upper liquid layer was aspired off, and seeds were washed 3 times with sterile water, followed by adding sterile water 2-fold the volume of the seeds. Seeds were suspension sowed in a screening medium (½ MS medium, 1% sucrose, 50 μg/mL Kanamycin, 50 μg/mL Cefotaxime, 0.7% agar, pH 5.7).

7. Histochemical Staining of GUS

Roots, stems, leaves, and inflorescences were clipped form *Arabidopsis* thialana transformant and were soaked first in a pre-treatment buffer [50 mM $Na_3PO_4$ (pH6.8), 1% TritonX-100] at 37° C. for 2 hours, followed by 2-3 times rinsed with a buffer solution (50 mM $Na_3PO_4$, pH 6.8) containing no Triton X-100. Then, a buffer solution (1 mM X-Gluc, dissolved in 50 mM $Na_3PO_4$, pH 6.8) containing X-Gluc (5-Bromo-4-chloro-3-indoxyl-beta-D-glucuronic acid) was added. The resulting mixture was treated at 25 inches-Hg vacuum for 5 minutes. Five minutes after being returned to atmospheric pressure, the procedure was repeated once more. Thereafter, the mixture was allowed to react at 37° C. for 2 days. Finally, 70% ethanol was added to terminate the enzymatic reaction and effected tissue discoloration. The color presentation thereof was observed under a microscope.

Results of GUS activity analysis were shown in FIG. 3. As shown in FIG. 3, reporter gene GUS activated by *Phalaenopsis* ACC synthase gene PtACS2 promoter demonstrated its expression only at petal, calyx and stamen of the floral organ in *Arabidopsis thialana* transgenic plant (as shown in FIG. 3D), while no GUS activity could be detected at the root, stem and leaf of *Arabidopsis thialana* transgenic plant (as shown in FIG. 3 A-C). It was shown from the result of GUS activity analysis that *Phalaenopsis* ACC synthase gene PtACS2 promoter exhibited expression specificity at floral organ tissues, and had significant activation ability.

Example 4

Transformation of *Nicotiana tabacum* L. by Employing *Agrobacterium*-Mediated Transformation Method In this example, *Nicotiana tabacum* L. (*Nicotiana tabacum* L. cv Wisc. 38) was used as the starting material and was subjected to a similar *Agrobacterium* transformation process to transfer plasmid pPtACS2-GUS prepared in Example 2 into *Nicotiana tabacum* L., while changing the genomic constitution of the transgenic plant such that *Phalaenopsis* ACC synthase gene PtACS2 promoter could activate effectively the expression of reporter gene GUS in the objective transgenic plant and progeny thereof. Furthermore, expression sites of reporter gene GUS at *Nicotiana tabacum* L. transgenic plant was analyzed by histochemical staining of GUS to detect whether *Phalaenopsis* ACC synthase gene PtACS2 promoter possessed tissue specificity in *Nicotiana tabacum* L. transgenic plant.

1. Preparation of *Agrobacterium* Liquor

This step was carried out as described in Example 3.

2. Transformation of *Agrobacterium*

This step was carried out as described in Example 3.

3. Mini-Preparation of *Agrobacterium* Plasmid after Transformation

This step was carried out as described in Example 3.

4. Transformation and Screening of *Nicotiana tabacum* L.

Leaves of aseptic sowed *Nicotiana tabacum* L. (*Nicotiana tabacum* L. cv Wisc. 38) plant was cut into squares of 1.5 cm×1.5 cm, which were placed over N01B1 solid culture medium (MS, 0.1 mg/L 1-naphthyl acetic acid, 1 mg/L BA, 3% sucrose, pH 5.7, 0.7% agar), and incubated at 25° C., in 16-hour light for 1 day. Thereafter, these leaf discs were immersed in the bacterial liquor for 3-5 minutes, and then placed over N01B1 solid culture medium. After being incubated at 25° C. in 16-hour light for 3 days, these leaf discs were rinsed by dipping in 20 mL N01B1 liquid culture medium containing 250 mg/L cefotaxime for 1 minute. Then, they were transferred onto N01B1 solid culture medium containing 250 mg/L Cefotaxime and 100 mg/L Kanamycin and were selected at 25° C. in 16-hour light for about 3 weeks. As adventitious shoots had shot from these leaf discs, they were transferred onto N01B1 solid culture medium containing 250 mg/l Cefotaxime and 200 mg/l Kanamycin, and were selected at 25° C. of 16-hour light. When shoots had grown to be longer than 1 cm, non-etiolated buds could be cut and cottage in MS solid culture medium containing 250 mg/L Cefotaxime and 200 mg/L Kanamycin and incubated at 25° C. in 16-hour light to permit root formation. Plant thereof was subjected to GUS activity assay.

5. Histochemical Staining of GUS

Roots, stem, leaves, and inflorescences were clipped form *Nicotiana tabacum* L. transformant, and were subjected to histochemical staining of GUS, respectively, following same process as described in Example 3.

Results of GUS activity analysis were shown as in FIG. 4. Reporter gene GUS activated by *Phalaenopsis* ACC synthase gene PtACS2 promoter could be expressed only at the petal, calyx and stamen in the floral organ of *Nicotiana tabacum* L. transformant (FIG. 4D), while no GUS activity could be detected at the root, stem and leaf of *Nicotiana tabacum* L. transformant (FIG. 4 A-C). From the results of GUS activity analysis for *Arabidopsis thialana* and *Nicotiana tabacum* L. transformants, it was demonstrated that *Phalaenopsis* ACC synthase gene PtACS2 promoter had indeed a characteristic of activating expression specifically in floral organ, and possessed significant activation ability.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. An isolated promoter for activating expression specifically in a floral organ tissue, characterized in that the isolated promoter comprises SEQ ID NO: 2.

2. A gene expression cassette, comprising:
   an isolated promoter, wherein the isolated promoter comprises SEQ ID NO: 2; and
   a polynucleotide having an open reading frame;
   wherein the polynucleotide is linked to the 3' end of the isolated promoter, and the isolated promoter can activate transcription of the polynucleotide in an organism containing the gene expression cassette.

3. A gene expression vector, comprising an isolated promoter, wherein the isolated promoter comprises SEQ ID NO: 2.

4. A method for producing a transgenic plant or parts of organ, tissue or cell of the transgenic plant that contain the gene expression cassette as recited in claim 2, said method comprising following steps:

step 1: taking cells or tissues of an objective plant;
step 2: transforming the gene expression cassette as recited in claim 2 into cells or tissues of the objective plant obtained in step 1 to produce a transgenic plant cell or transgenic plant tissue; and
step 3: cultivating the transgenic plant cell or transgenic plant tissue obtained in step 2 to produce a transgenic plant or part of organ, tissue or cell of said transgenic plant containing the gene expression cassette as recited in claim 2.

5. The method as recited in claim 4, wherein transforming the gene expression cassette described in step 2 is achieved by a method selected from the group consisting of *Agrobacterium tumefaciens*-mediating method, gene recombinant virus infection method, transposon vector transfection method, gene gun transformation method, electroporation method, micro-injection method, pollen tube pathway, liposome-mediated transformation method, ultrasonic-mediated transformation method, silicon carbide fiber-mediated transformation, electrophoresis, laser microbeam, polyethylene glycol (PEG), calcium phosphate transformation, and DEAE-dextran transformation.

* * * * *